United States Patent
Gao et al.

(10) Patent No.: US 10,406,000 B2
(45) Date of Patent: Sep. 10, 2019

(54) ANKLE-FOOT PROSTHESIS DEVICE

(71) Applicant: The Chinese University of Hong Kong, Shatin, N.T., Hong Kong (CN)

(72) Inventors: Fei Gao, Neijiang (CN); Yan-Nan Liu, Wuxue (CN); Wei-Hsin Liao, Ma On Shan (CN)

(73) Assignee: The Chinese University of Hong Kong, Shatin, N.T., Hong Kong (CN)

( * ) Notice: Subject to any disclaimer, the term of this patent is extended or adjusted under 35 U.S.C. 154(b) by 0 days.

(21) Appl. No.: 15/280,788

(22) Filed: Sep. 29, 2016

(65) Prior Publication Data
US 2018/0085237 A1     Mar. 29, 2018

(51) Int. Cl.
| | | |
|---|---|---|
| A61F 2/66 | (2006.01) | |
| A61F 2/68 | (2006.01) | |
| A61F 2/70 | (2006.01) | |
| A61F 2/76 | (2006.01) | |
| A61F 2/50 | (2006.01) | |

(52) U.S. Cl.
CPC .............. *A61F 2/6607* (2013.01); *A61F 2/66* (2013.01); *A61F 2/68* (2013.01); *A61F 2/70* (2013.01); *A61F 2002/5009* (2013.01); *A61F 2002/5075* (2013.01); *A61F 2002/6664* (2013.01); *A61F 2002/701* (2013.01); *A61F 2002/704* (2013.01); *A61F 2002/7625* (2013.01); *A61F 2002/7635* (2013.01); *A61F 2002/7645* (2013.01)

(58) Field of Classification Search
CPC .. A61F 2/6607; A61F 2/60; A61F 2/66; A61F 2/68
See application file for complete search history.

(56) References Cited

U.S. PATENT DOCUMENTS

| | | | | |
|---|---|---|---|---|
| 7,485,152 | B2* | 2/2009 | Haynes | A61F 2/64 623/24 |
| 8,512,415 | B2* | 8/2013 | Herr | A61F 2/60 623/24 |
| 2014/0296997 | A1* | 10/2014 | Herr | A61F 5/0111 623/24 |
| 2015/0202057 | A1* | 7/2015 | Zahedi | A61F 2/64 623/26 |

FOREIGN PATENT DOCUMENTS

CN     201564637 U    9/2010

\* cited by examiner

*Primary Examiner* — Marcia L Watkins
(74) *Attorney, Agent, or Firm* — Kilpatrick Townsend & Stockton LLP (57) ABSTRACT

A powered ankle-foot prosthesis and associated methods of use are described herein. Such prostheses can employ an actuator and elastic components, the actuator being controlled to deliver net positive work to propel the wearing amputee forward and the elastic components being used to store and release negative energy to improve efficiency. Elastic components can be linear springs coupled with a cam and configured in parallel to the actuator. The cam profile can be designed to generate a desired spring torque versus angle curve rather than a spring stroke versus angle curve, thereby reproducing human ankle controlled dorsiflexion stiffness. Such configurations improve system energy efficiency and reduce both actuator torque and power requirements. Such prostheses can also operate in a passive mode, in which a nearly normal gait can be achieved even without powered assist.

17 Claims, 12 Drawing Sheets

ANKLE-FOOT PROSTHESIS DEVICE

BACKGROUND

Ankle-foot prostheses, also known as transtibial prostheses, are used to help regain walking function in individuals having amputations below the knee. Existing commercial transtibial prostheses generally can be classified into two main types: passive transtibial prostheses and powered transtibial prostheses. As passive transtibial prostheses do not contain actuators, these cannot provide net positive work during a gait cycle, as does an intact human ankle. This lack of positive work hinders amputees from restoring a more natural gait behavior. For some passive prostheses, spring-clutch mechanisms can be used to adjust ankle angle in walking, or improve metabolic walking economy. However, clinical studies showed that due to the inability of passive prostheses to supply net positive work across the stance, transtibial amputees with passive prostheses have various problems during walking, such as non-symmetric gait patterns and higher metabolic cost as compared to the gait of intact individuals.

For powered prostheses, actuators are employed to deliver net positive energy to propel the body forward during walking. This decreases the amputees' effort in walking or metabolic cost significantly and, in addition, allows more normal gaits to be achieved. However, powered prostheses present certain challenges. The two main issues are the use of actuators and power. Although motors are widely used in prostheses. It is difficult to provide the required maximum torque while meeting size and weight requirements. For example, for a 75 kg male person, the ankle-foot complex weighs about 2 kg. During walking, the maximum torque and power would reach 120 Nm and 320 W, respectively. Commercial batteries (e.g., lithium-polymer battery) are usually used for powering prostheses. The battery should provide the energy needed for daily walking. However, with the battery energy density limitation, most commercial batteries cannot supply the energy consumption for an entire day without battery recharge/replacement while meeting the size and weight requirements for an ankle-foot prosthesis.

In some conditions, the batteries cannot supply the enough energy for the powered prostheses due to the excessive walking of the amputees. The powered prostheses will work in passive mode. In that case, we hope the powered prostheses also can reproduce some function of intact ankle, to achieve a relatively normal gait.

BRIEF SUMMARY

In one aspect, the invention provides an ankle-foot prosthesis that employs an actuator in combination with elastic elements used to store and release negative mechanical energy. As a result, the system energy consumption can be decreased significantly. In addition, the torque and power requirements of the actuator are also reduced, which further allows the battery and the motor to be downsized.

In some embodiments, the powered ankle-foot prosthesis employs an actuator and elastic components. The actuator is controlled to deliver net positive work that propels the wearing amputee forward. The elastic components are embodied as a spring mechanism, such as linear springs, which are coupled with a cam and configured in parallel to the actuator. Herein, the cam profile is designed to generate desired spring torque versus angle curve rather than the spring stroke versus angle curve. In such a case, the spring can reproduce human ankle controlled dorsiflexion stiffness. As a result, control of the motor is not needed in controlled dorsiflexion phase. Further, the system energy efficiency is improved and both the actuator torque and power requirements are reduced. In addition, the parallel spring configuration can reproduce the required torque during dorsiflexion and then release the energy to propel amputees forward in push-off phase, so that the present prosthesis can achieve a nearly normal gait even when working in a passive mode.

Embodiments of the design of the cam profile are introduced in detail. The profile is decomposed in several segments. Each segment is approximated by the third-order polynomial. In some embodiments, to make the real torque-angle curve close to the desired curve, the cam profile should be convex.

In some embodiments, a controller for the prosthesis is present, in which a finite state machine is used. Multiple sensors, including an angle sensor for detecting ankle angle and a flexible force sensor for measuring the prosthesis axial force, are used to obtain the real-time information for controller.

The following figures and descriptions are presented below to further illustrate various aspects of the invention. It is appreciated that the invention is not limited to the embodiments described below and encompasses various alternative embodiments and variations as would be understood by one of skill in the art.

DETAILED DESCRIPTION

Embodiments of the present invention relate to powered ankle-foot prosthesis utilizing an actuator in combination with elastic components. The invention is minutely described with reference to the attached figures; the reference numerals are used to designate similar elements.

FIGS. 1-4 shows an embodiment of an ankle-foot prosthesis in accordance with the inventive aspects described herein. An elastic foot 16 is used for shock absorption during a heel-strike portion of a gait. The elastic foot 16 can be embodied as a carbon fiber foot, or any suitable material of sufficient strength and weight for use in an ankle-foot prosthesis. As described herein, elastic foot refers to any type of shock-absorbing foot which can utilize various types of features or mechanisms (e.g. elastomers, spring mechanism, resilient blade, piston, etc.). The ankle-foot prosthesis includes a foot mount 20 for attaching elastic foot 16. Foot mount 20 can include a planar surface with a threaded hole through which a fastening bolt 21 is inserted to securely fasten shock-absorbing foot 16 onto the prosthesis. Mount 20 can include one or more orienting features (e.g. interfacing features, grooves, contours, pegs and holes) configured to secure elastic foot 16 into its proper orientation when mounted. It is appreciated that in various embodiments, foot mount can be configured in other sizes and shapes (e.g. a contoured region, cylinder) and include any suitable means for securely fastening elastic foot to the prosthesis (e.g. clips, socket, snap-fit, interference fit, fasteners, etc.). An adapter 12 is used for attaching a socket interface for coupling to a residual lower limb of the amputee.

As shown in FIGS. 1-4, an angle sensor 5 is mounted on the ankle joint 39 for detecting a prosthesis ankle angle, the ankle joint 39 joining shin bracket 11 to bracket support foot 8. The angle sensor 5 can be embodied as a potentiometer or a hall angular sensor, or any suitable sensor. A force sensor 30 is installed between adaptor 12 and shin bracket 11 for measuring a prosthesis axial force. The force sensor 30 can be embodied as a force-sensing resistor (FSR), or any suitable force sensor. An elastic spacer 31 is used to protect force sensor 30. Power supply 33 is placed in the battery holder 34 and used for powering the prosthesis. Power supply 33 can be embodied as a lithium-polymer battery, or any suitable battery or power source. Cover 32 for protecting electronic circuits is mounted on shin bracket 11.

In some embodiments, the driving mechanism for the prosthesis includes two parts: a motor drive unit and a parallel spring mechanism. The motor drive unit contains a DC motor 4, a timing-belt transmission (timing pulleys 35, 36, timing belt 37) and a ball-screw nut transmission (ball-screw 2, ball nut 1, ball nut holder 9 coupled to bracket support 8 via pin 25, bearing 3, and bearing holder 10 coupled to shin bracket 11 via pin 26), as shown in the exploded view of FIG. 2. This part is designed to deliver net positive work to embodiments of the ankle-foot prosthesis through a slider-crank linkage.

Figure 1:
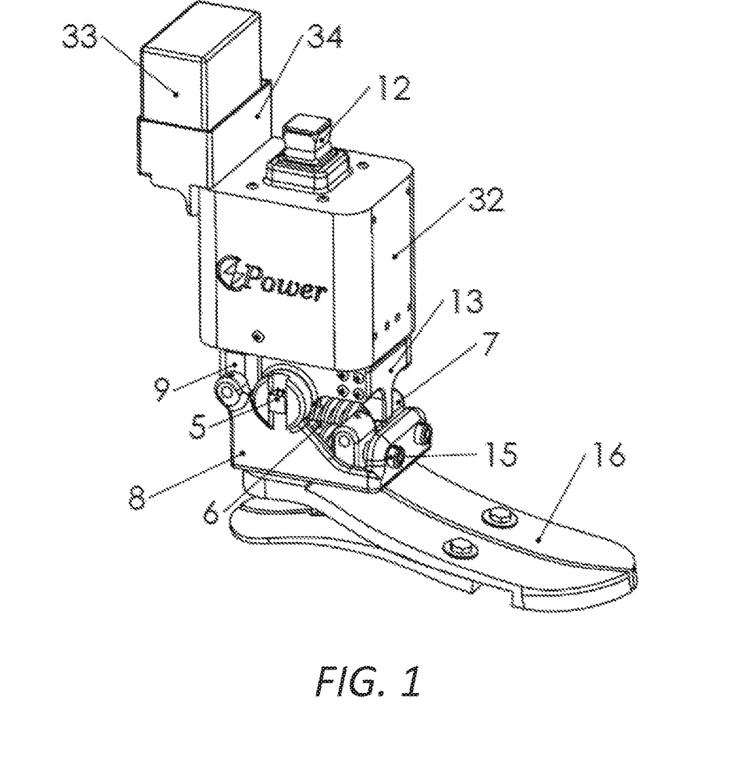
FIG. 1 is front perspective view of a powered ankle-foot prosthesis, according to an embodiment of the invention.
Figure 2:
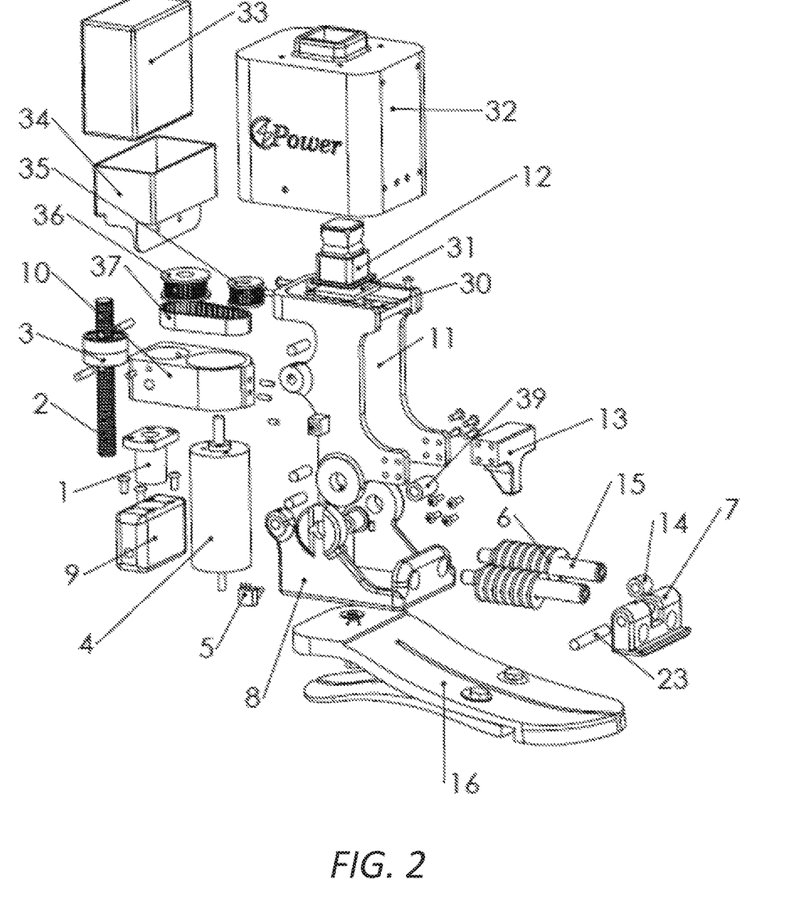
FIG. 2 is an exploded view of a powered ankle-foot prosthesis, according to an embodiment of the invention.
Figure 3:
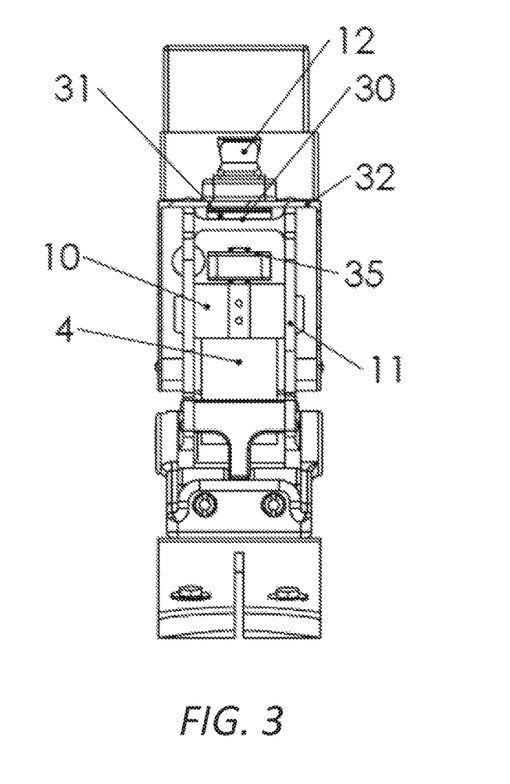
FIG. 3 is a front part sectional view of a powered ankle-foot prosthesis, according to an embodiment of the invention.
Figure 4:
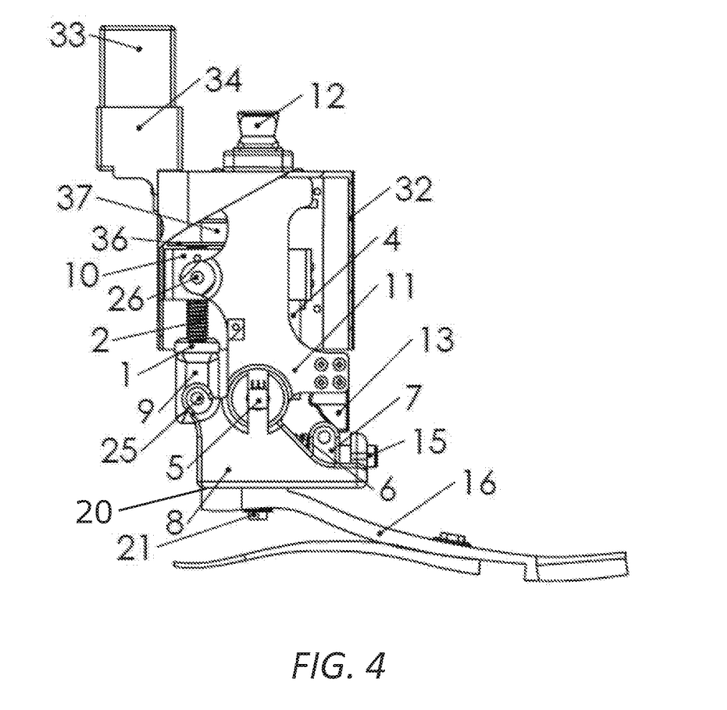
FIG. 4 is a side part sectional view of a powered ankle-foot prosthesis, in accordance with an embodiment of the invention.
Figure 5:
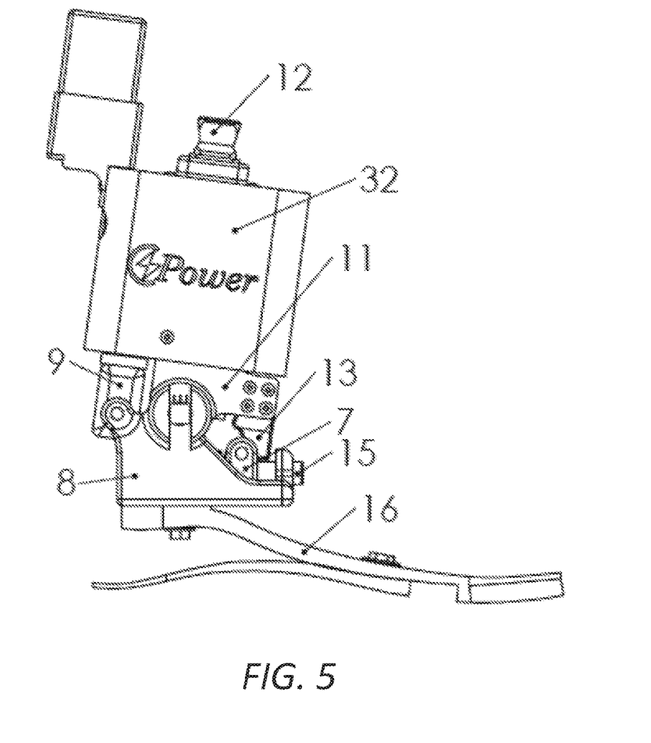
FIG. 5 is a side view of a powered ankle-foot prosthesis, in accordance with an embodiment of the invention.

In this embodiment, the parallel spring mechanism includes two linear springs 6, a cam 13, a slider 7 and two rods 15. The slider 7 and linear springs 6 are mounted on the rods 15. A roller 14, held in slider 7 by pin 23, is used to reduce the friction force between cam 13 and slider 7. When the upper body rotates clockwise (in dorsiflexion) as shown in FIG. 5, the cam 13 pushes the slider 7 to compress the linear springs 6. As a result, a torque is generated on the prosthetic ankle 39. Here, by designing the cam profile, the desired spring torque versus angle curve will be obtained.

Ankle-Foot Prosthesis Model

The instantaneous output torque of embodiments of the ankle-foot prosthesis equals to the sum of motor output torque and spring torque.

$$\tau = \tau_m + \tau_p \quad (1)$$

where $$\tau_m = i_m K_t R - M_e \ddot{\theta} - b \dot{\theta} \quad (2)$$

$$i_m = \left(u_b K_u - \frac{\dot{\theta}}{K_e}\right) / R_m \quad (3)$$

$$\tau_p = \begin{cases} 0, & \theta \leq 0 \\ f(\theta), & \theta > 0 \end{cases} \quad (4)$$

where $u_b$ is battery voltage. $K_u$ ($0 \leq K_u \leq 1$) is a coefficient, which is related to motor control signal. $i_m$ is motor current. $K_e$, $K_t$ and $R_m$ are motor speed constant, torque constant and resistance, respectively. $M_e$ ($M_e = I_m R^2$) refers to effective mass. $b_e$ ($b_e = b_m R$) is effective damping coefficient. $I_m$, $b_m$ refer to motor rotary inertia and motor friction, respectively. R is the transmission ratio. $\theta$ is ankle angle. $f(\theta)$ is related to spring stiffness and cam profile. As shown in the prosthesis model equations (1)-(4), the maximum output torque of prosthesis at any angle $\theta$ is determined not only by the motor control signal $K_u$ but also by the angular velocity $\dot{\theta}$ and angular acceleration $\ddot{\theta}$.

Design of Spring Torque Versus Angle Curve

In some embodiments of the prosthesis, parallel springs are used to store and release negative mechanical energy. As a result, system energy efficiency is improved, and the motor torque and power requirements are reduced due to the supplemental torque from parallel springs.

Figure 6:
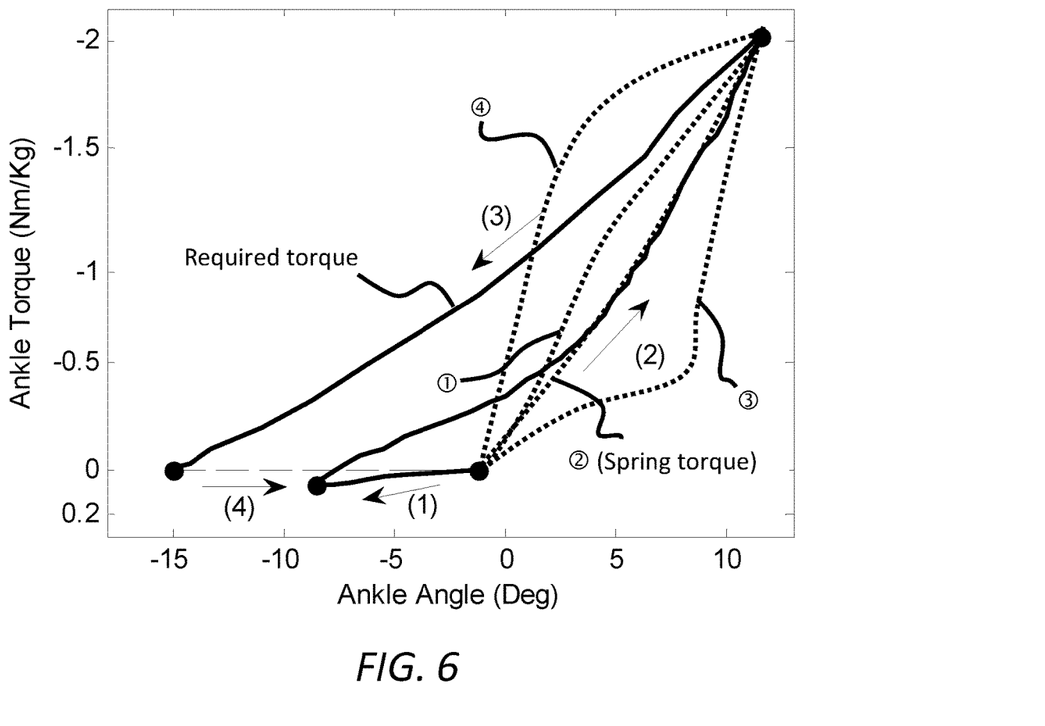
FIG. 6 is a plot of unit torque versus ankle angle, in accordance with an embodiment of the invention.
Figure 7A:
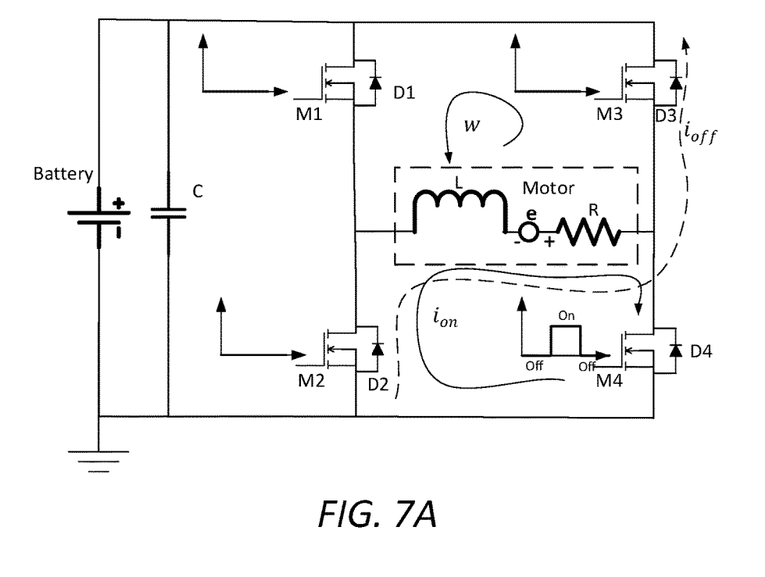
FIGS. 7A and 7B are the working principles of the drive circuit for the actuator in initial controlled dorsiflexion, in accordance with an embodiment of the invention.
Figure 7B:
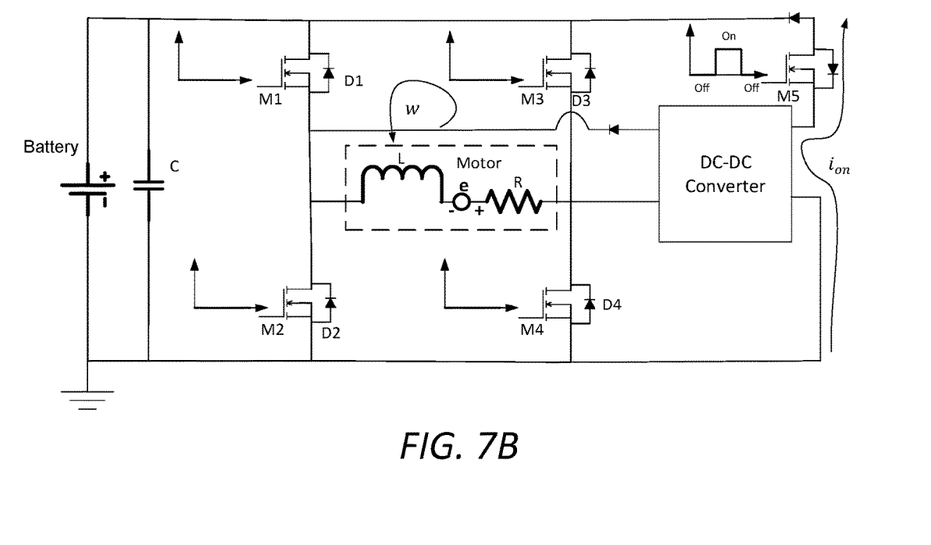

In some embodiments, the prosthesis is configured and controlled to selectively provide required torques during a portion of the gate to allow for a more natural gate. For example, the prosthesis can be configured to provide a torque during controlled dorsiflexion (CD) and powered plantarflexion (PP). In the embodiments depicted, to ensure the prosthesis rotates freely during swing phase, the parallel springs are engaged only when ankle angle is larger than zero, as shown in FIG. 6. In such embodiments, the spring torque is smaller than the required torque in initial CD. Therefore, the DC motor 4 is used to generate a damping torque in this phase. The working principles of the drive circuit for DC motor 4 is shown in FIG. 7A. In some embodiments, a PWM signal is used to control M4 for adjusting motor damping torque. In this process, some negative mechanical energy is converted to electrical energy and stored in the battery 33. Note that some energy will be dissipated in the conversion process. To improve the conversion efficiency, a DC-DC converter can be used in the drive circuit FIG. 7B.

In some embodiments, in the design of parallel spring torque versus angle curve, there are at least four cases, as shown in FIG. 6. For case ①, the spring torque is between the required torque in CD and PP. As the required torques are smaller than the spring torques in CD, the motor is powered to compress the parallel springs. Then in PP, the motor is also powered to supply the extra torque to propel the amputee forward.

For case ②, the spring torque equals to the required torque in CD. In this case, the motor is powered off and there is no control during late CD. In PP, the motor works substantially the same as in case ①. The total energy consumption in case ② substantially equals to that in case ①.

For case ③, the spring torque is smaller than the required torque in CD. Some negative mechanical energy is not stored in the springs. As angular velocity is very small in late CD, the negative mechanical energy cannot be converted to electrical energy, and is consumed by the motor. In this case, the system energy efficiency is lowered. In PP, the motor works substantially the same as in cases ① and ②.

For case ④, the spring torque is larger than the required torque in PP. The motor works substantially the same as in case ① in late CD. While in PP, the required torque is smaller than spring torque. Some mechanical energy is converted to electrical energy. As mentioned before, some mechanical energy will be consumed during conversion. As a result, the system energy efficiency is decreased.

In summary, cases ① and ② have substantially the same energy efficiency that is higher than that in cases ③ and ④. Note that the motor is powered off during late phase CD in case ②, which simplifies the control of the prosthesis. In addition, when the battery is used up, the amputee with the prosthesis can have a more normal gait in case ② than other cases. Based on the above analysis, the spring torque versus angle curve in some embodiments of the prosthesis will be designed according to case ②.

It is appreciated that in any of the embodiments above, variations can be realized, for example certain aspects described in one case can be modified or substituted for certain aspects described in another case as desired

Cam Profile Design

Figure 8:
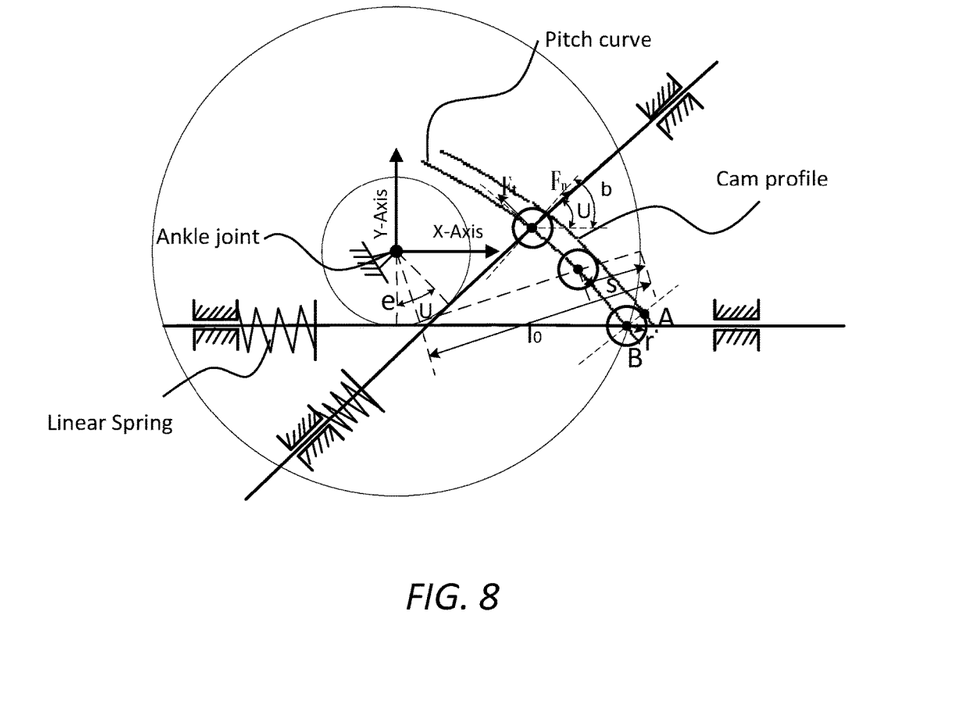
FIG. 8 is a geometric model of the cam for use in a powered ankle-foot prosthesis, in accordance with an embodiment of the invention.

In this invention, the cam profile is designed to generate desired spring torque versus angle curve rather than the spring stroke versus angle curve. The geometric model of the cam is shown in FIG. 8, and cam profile $f(x_A, y_A)$ can be derived as follows:

$$x_A = x_B + r \frac{dy_B/d\theta}{\sqrt{\left(\frac{dy_B}{d\theta}\right)^2 + \left(\frac{dx_B}{d\theta}\right)^2}} \quad (5)$$

$$y_A = y_B - r \frac{dx_B/d\theta}{\sqrt{\left(\frac{dy_B}{d\theta}\right)^2 + \left(\frac{dx_B}{d\theta}\right)^2}} \quad (6)$$

where $f(x_B, y_B)$ is the pitch curve. r is radius of roller 14, as shown in FIG. 8.

The spring torque is given by:

$$\tau_p = F_\tau(l_0 - s) + F_n e \quad (7)$$

where $$F_n = ks + \mu F_\tau \text{sgn}(\dot{s}) \quad (8)$$

$$F_\tau = F_n \tan(\beta - \theta) = F_n \frac{\tan\beta \cos\theta - \sin\theta}{\cos\theta + \tan\beta \sin\theta} \quad (9)$$

$$\tan\beta = -\frac{1}{k_{x_B}} \quad (10)$$

where k is stiffness of general compression springs 6. s is deformation of general compression springs 6. e is an offset of the roller from the rotary center of the cam (ankle joint). μ is a friction coefficient between slider 7 and rods 15. β and θ are shown as in FIG. 8. $k_{x_B}$ is the curve slope.

Figure 9:
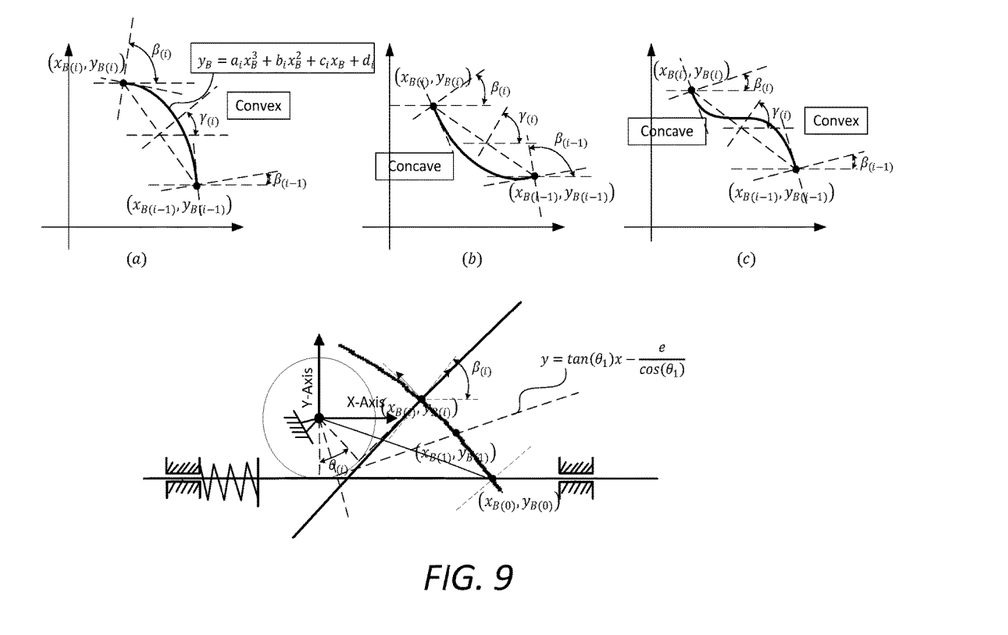
FIG. 9 is the design of the cam profile, in accordance with an embodiment of the invention.

In the design process, the spring torque versus angle curve can be decomposed in n segments. In this embodiment, n is set to 4, and the corresponding segment points are set as [(0, 0), $(\theta_1, \tau_{p1})$, $(\theta_2, \tau_{p2})$, $(\theta_3, \tau_{p3})$, $(\theta_4, \tau_{p4})$]. The cam profile is also divided into 4 segments. Each segment in the cam profile is approximated by the third-order polynomial as shown in FIG. 9, which can ensure cam profile slope continuance on the segment points. It is appreciated that the curve could be decomposed in more or less segments and similar concepts applied.

$$y_B = a_i x_B^3 + b_i x_B^2 + c_i x_B + d_i (i=1, \ldots 4) \quad (11)$$

According to equations (7)-(9), the spring torque is determined by spring stiffness k, friction coefficient μ, spring deformation s, and β. In practice, the k and μ are preset. μ is determined by machining precision, and k can be changed by choosing different spring models. Thus, the spring torque can be expressed as a function, $\tau_s = f(s, \beta)$. For each segment point of pitch curve, firstly the spring deformations is preset. then the corresponding β at the segment point can be derived as follows:

$$\tan(\beta) = \frac{A\cos(\theta_1) + \sin(\theta_1)}{\cos(\theta_1) - A\sin(\theta_1)} \quad (12)$$

where A is defined in equation (13).

$$A = \frac{\tau_{p1} - ks_1 e}{ks_1(l_0 - s_1) + \tau_{p1}\mu\text{sgn}(\dot{s})} \quad (13)$$

In equation (13), the sgn($\dot{s}$) is set to be the same as sgn($s_1 - s_0$) for simplifying the calculation. The parameters in the third-order polynomial are obtained.

$$CC = [a_i, b_i, c_i, d_i]^T \quad (14)$$

$$CC = AA^{-1} * BB \quad (15)$$

where AA and BB are defined as follows:

$$AA = \begin{bmatrix} x_{B(i-1)}^3 & x_{B(i-1)}^2 & x_{B(i-1)} & 1 \\ x_{B(i)}^3 & x_{B(i)}^2 & x_{B(i)} & 1 \\ 3x_{B(i-1)}^2 & 2x_{B(i-1)} & 1 & 0 \\ 3x_{B(i)}^2 & 2x_{B(i)} & 1 & 0 \end{bmatrix} \quad (16)$$

$$BB = \left[ y_{B(i-1)}, y_{B(i)}, k_{x_{B(i-1)}}, k_{x_{B(i)}} \right]^T \quad (17)$$

where $$x_{B(i)} = (l_0 - s_i)\cos\theta_{(i)} + e\sin\theta_{(i)} \quad (18)$$

$$y_{B(i)} = (l_0 - s_i)\sin\theta_{(i)} - e\cos\theta_{(i)} \quad (19)$$

Figure 10A:
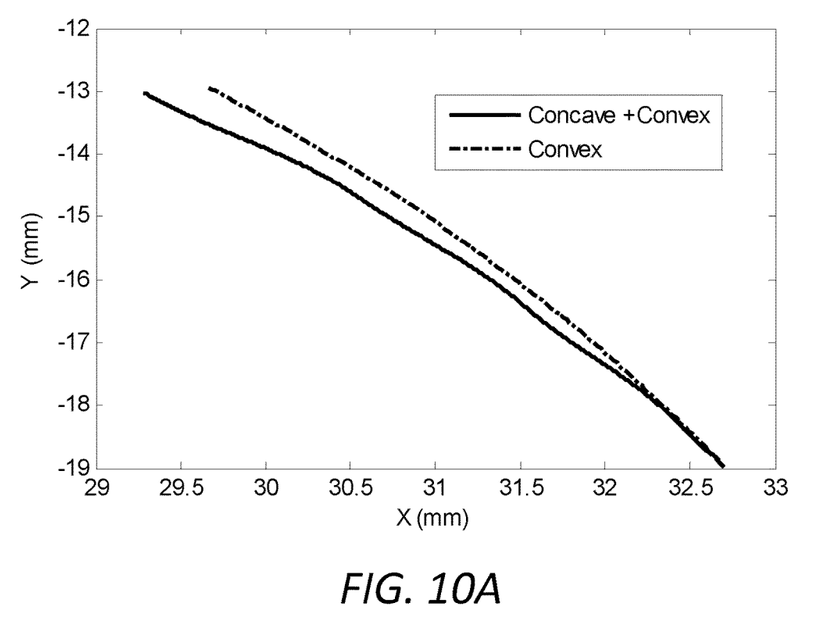
FIGS. 10A and 10B depict the cam pitch curve and the spring torque versus angle curve, respectively, in accordance with an embodiment of the invention.
Figure 10B:
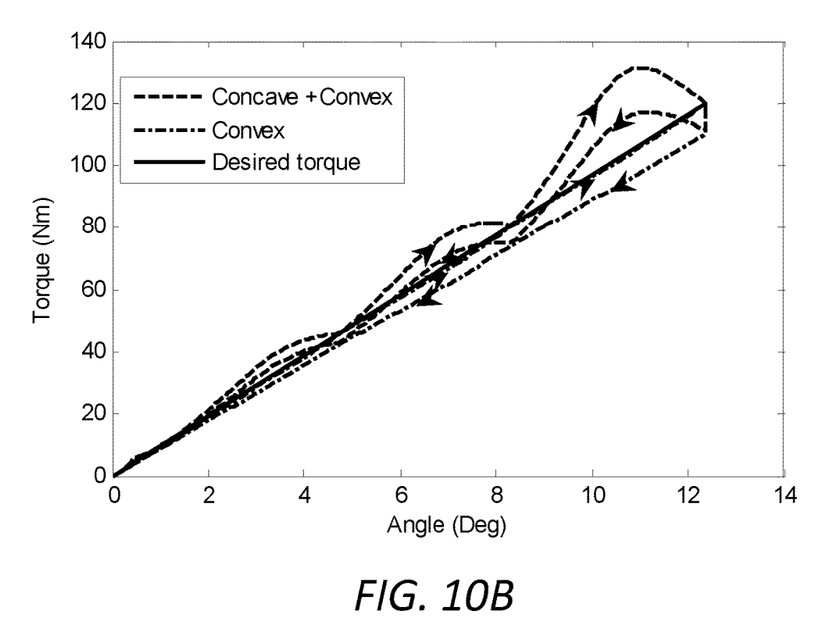

In some embodiments, there are generally three types of pitch curve segments: convex, concave, and convex+concave. Examples of such segments are shown in FIG. 9. For the first and second types, the slopes of pitch curve have a relatively small change in one segment. While for the last type, the slopes may encounter a larger change. This will introduce a large variation in the spring torque, as shown in FIGS. 10A and B, since the spring torque is related to the pitch curve slopes, according to equations (7)-(10).

In such embodiments, the cam profile is designed to be convex curve, and the follow condition is used to improve the possibility of being convex curve.

$$\beta_{(i-1)} < \gamma_{(i)} < \beta_{(i)} \quad (20)$$

Each segment can be approximated by a third-order polynomial. Note that when the above condition is satisfied, the pitch curve also can be concave+convex.

In one aspect of the he design process, to avoid undercutting when designing the cam profile, the curvature radius $\rho_{x_B}$ of $f(x_B, y_B)$ should satisfy the condition:

$$\min(\rho_{x_B}) > r, \text{ if } f(x_B, y_B) \text{ is concave} \quad (21)$$

In another aspect of the design process, to enable slider 7 move along rods 15, $(\beta-\theta)$ should be smaller than the frictional angle $\varphi_m$.

$$\text{abs}(\beta-\theta) < 90° - \varphi_m \quad (22)$$

Note that as shown in FIG. 10B, there is small difference between the spring torques in CD phase and push-off phase. That is induced by the friction force between slider 7 and rods 15. Some mechanical energy will be dissipated by the friction force. By reducing $(\beta-\theta)$ or the friction coefficient $\mu$, the difference can be decreased.

It is appreciated that certain embodiments may include only some of the aspects described herein or modification of these aspects in order to provide a desired performance. For example, some amputees may have limitations in movement necessitating a prosthesis with limited or specialized movement.

Controller Design

Figure 11:
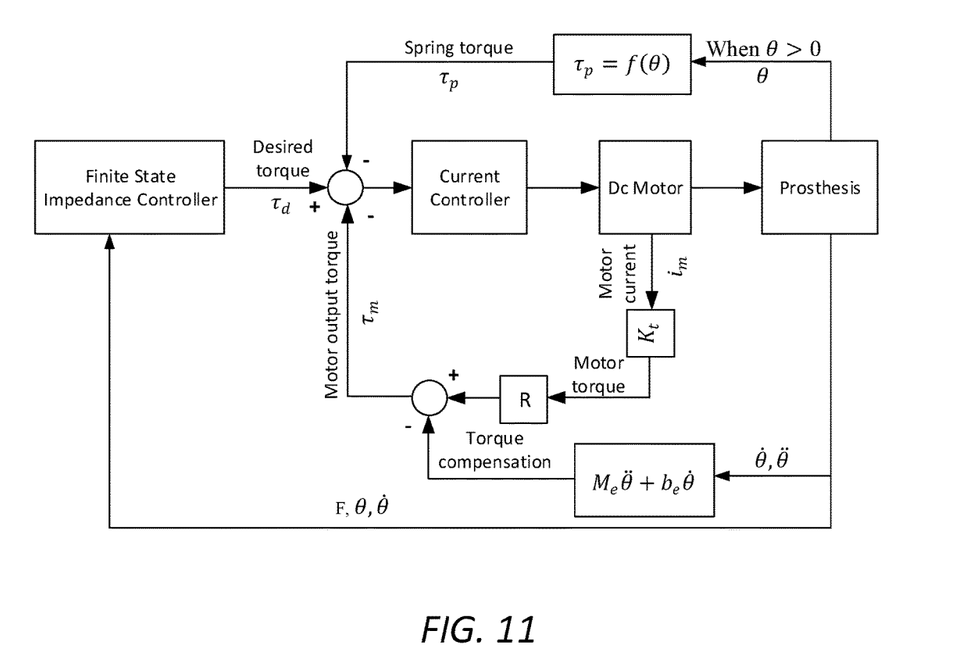
FIG. 11 shows a block diagram for the controller, in accordance with an embodiment of the invention.

In this section, an example controller for controlling the ankle-foot prosthesis is shown in FIG. 11. The controller is configured to provide torque trajectories rather than position trajectories for the prosthesis. In such configurations, the motion of prosthesis is resulted from the interaction of the wearing amputee and the prosthesis, so as to provide a more natural human gait. The reference torque is governed by a finite state machine, as shown in FIG. 12.

In the described embodiment, the motor output torque is not directly detected by torque or force sensors. Herein, it is derived by motor model in equation (2) and motor current $i_m$, which is detected by sampling resistances. Although certain error exists between the derived torque and actual torque, it is acceptable in practice. In the controller, a current controller is used to adjust the motor current. The current controller can be embodied as a PD controller. It is appreciated that in various other embodiments, one or both of the motor output torque could be detected by one or more sensors.

Figure 12:
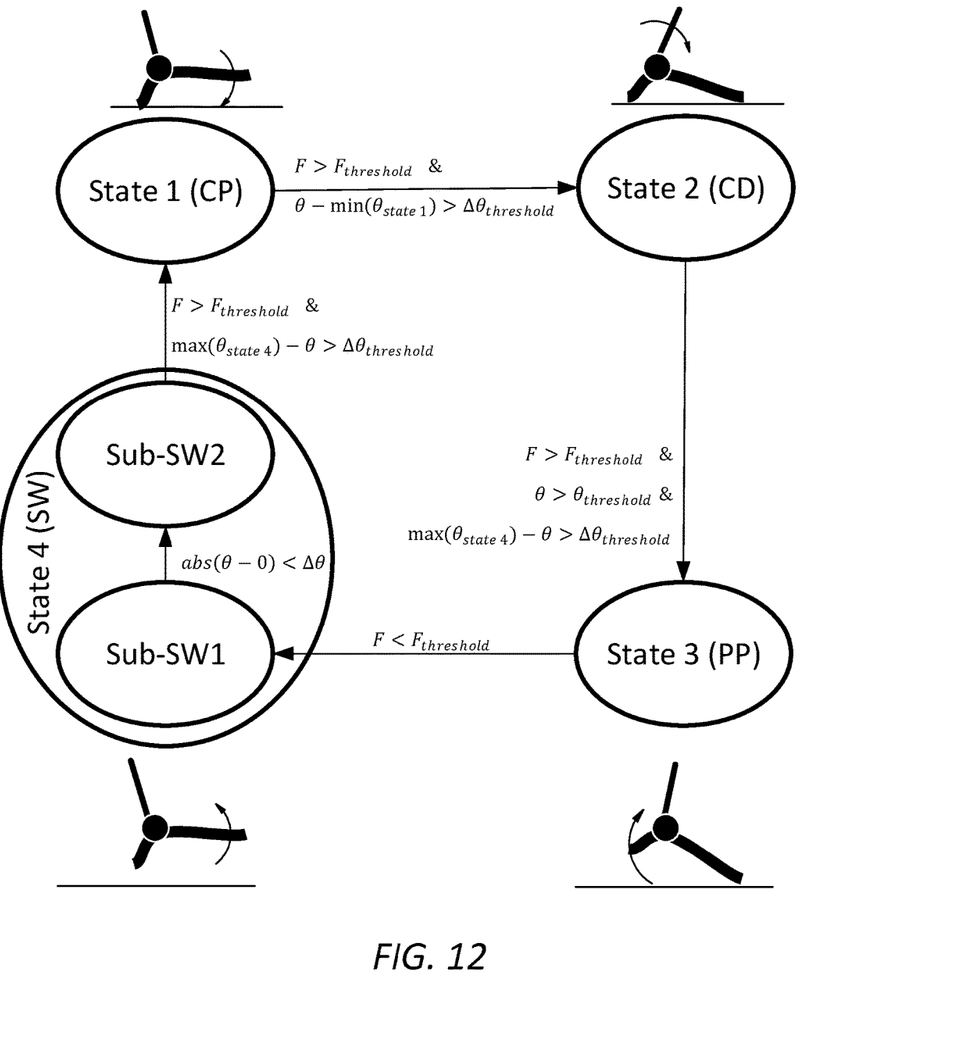
FIG. 12 shows a finite state machine, in accordance with an embodiment of the invention.

In the finite state machine shown in FIG. 12, one gait cycle is divided into four states. Note that the state (4) includes two sub-phases. In the Sub-SW2 phase, the system is be reset. The input signals contain force and angle signals. Force signals are used to distinguish stance phase (states 1-3) from swing phase (state 4). Angular velocity ($\dot{\theta}$) is replaced by an angle threshold ($\Delta\theta_{threshold}$) to improve anti-interference performance.

It is appreciated that the invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. Variations and modification made by those skilled in the art according to the disclosure herein should be within the scope of the present invention.

What is claimed is:

1. A powered ankle-foot prosthetic device for restoring a required ankle torque for a gait to an amputee wearing the prosthetic device, the prosthetic device comprising:
   an ankle joint that defines an ankle angle between a shin bracket and a bracket support foot;
   a motor operably coupled to the ankle joint, wherein the motor is configured to:
      selectively provide a motor torque output to achieve the required ankle torque during phases of the gait, wherein selectively providing the motor torque output comprises:
         providing the motor torque output during an initial phase of a controlled dorsiflexion phase;
         providing the motor torque output during swing phase;
         and
         providing the motor output torque in a powered plantar flexion phase of a stance phase; and
   a parallel spring mechanism including a cam operably coupled with the ankle joint in parallel with the motor, wherein the parallel spring mechanism is configured to:
      provide a spring torque output during the controlled dorsiflexion phase and
   wherein the prosthetic device is configured such that the spring torque output and the motor torque output provide the required ankle torque that produces a curved torque versus ankle angle plot during the controlled dorsiflexion phase.

2. The device of claim 1, wherein the cam is attached to the shin bracket, wherein the parallel spring mechanism further includes a slider, a roller, rods, and springs such that when the shin bracket rotates, engagement of the cam with the slider varies the spring torque output producing the curved ankle torque versus ankle angle plot.

3. The device of claim 2, wherein the cam is configured to compress the springs thereby generating the spring torque output, when the ankle angle of the ankle joint of the prosthetic device is larger than zero, zero being when the shin bracket is perpendicular to the bracket support foot.

4. The device of claim 3, wherein the cam is configured to operate according to a cam profile that is decomposed in a plurality of segments.

5. The device of claim 4 wherein a pitch curve slope of each segment of the cam profile is approximated by a third-order polynomial.

6. The device of claim 4, wherein a pitch curve slope of each segment of the cam profile is a convex curve.

7. The device of claim 2, wherein the cam is configured to operate according to a cam profile with several cam pitch curve slopes that are achieved based on a stiffness of the parallel spring mechanism which ensures the parallel spring mechanism produces the curved ankle torque versus ankle angle plot during the controlled dorsiflexion phase of the gait of the amputee.

8. The device of claim 2, wherein the roller is an offset roller, and wherein the cam is operably engaged with the springs via the offset roller and slider.

9. The device of claim 2, wherein the cam is configured to operate according to a cam profile with several pitch curve slopes.

10. The device of claim 2, wherein the cam is configured to operate according to a cam profile, wherein the cam profile comprises one or more of: a convex segment, a concave segment, and a convex-concave segment.

11. The device of claim 1, wherein the curved ankle torque versus ankle angle plot extends between an ankle torque of 0 Nm/Kg and 2 Nm/Kg.

12. The device according to claim 1, further comprising a DC-DC converter configured to improve an induced voltage of the motor in the prosthetic device for charging a battery when the motor works as a generator to harvest a negative mechanical energy during some phases of the gait of the amputee.

13. The device of claim 1,
wherein the prosthetic device is configured to operate in both a powered mode and a passive mode, the prosthetic device having a total output torque at the ankle angle joint at any given time,
wherein in the passive mode, the total output torque includes only the spring output torque of the parallel spring mechanism; and
in the powered mode, the total output torque includes the motor output torque in addition to the spring output torque of the parallel spring mechanism.

14. The device of claim 13, wherein the motor is configured to provide a damping torque during the initial phase of the controlled dorsiflexion.

15. The device of claim 1,
wherein the parallel spring mechanism is configured to engage only when the ankle angle is larger than zero, zero being when the shin bracket is perpendicular to the bracket support foot, to ensure the prosthetic device rotates freely during the swing phase.

16. The device of claim 1, further comprising:
an ankle angle sensor configured for detecting the ankle angle between the shin bracket and the bracket support foot; and
a controller in communication with an output of the ankle angle sensor, the controller configured for distinguishing between gait phases of the amputee based, at least in part, on the output of the ankle angle sensor,
wherein the prosthetic device is configured such that:
after an initial phase of the controlled dorsiflexion phase, a total torque output of the prosthetic device is provided by the spring torque output of the parallel spring mechanism without any motor torque output;
when the powered plantarflexion phase of the stance phase is indicated, the total torque output of the prosthetic device is provided by the motor output torque in addition to the spring torque output of the parallel spring mechanism.

17. The device of claim 16, further comprising:
a force sensor arranged and configured for measuring prosthetic axial force applied by the amputee on the prosthetic device,
wherein the controller is in communication with an output of the force sensor and configured to distinguish between gait phases of the amputee based, at least in part, on the outputs of the force sensor and the ankle angle sensor.

* * * * *